(12) United States Patent
Laredo

(10) Patent No.: US 8,557,892 B2
(45) Date of Patent: Oct. 15, 2013

(54) HYDROPHOBIC ACRYLIC INTRAOCULAR LENS MATERIALS

(75) Inventor: Walter R. Laredo, Fort Worth, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/486,797

(22) Filed: Jun. 1, 2012

(65) Prior Publication Data

US 2012/0309919 A1   Dec. 6, 2012

Related U.S. Application Data

(60) Provisional application No. 61/493,114, filed on Jun. 3, 2011.

(51) Int. Cl.
| | | |
|---|---|---|
| *G02B 1/04* | (2006.01) | |
| *B29D 11/00* | (2006.01) | |
| *C08F 290/06* | (2006.01) | |
| *A61F 2/16* | (2006.01) | |

(52) U.S. Cl.
USPC ........... 523/106; 523/107; 523/108; 623/6.11

(58) Field of Classification Search
USPC .......................... 523/106, 107, 108; 623/6.11
See application file for complete search history.

(56) References Cited

U.S. PATENT DOCUMENTS

| | | | |
|---|---|---|---|
| 4,834,750 A | 5/1989 | Gupta | |
| 5,290,892 A | 3/1994 | Namdaran et al. | |
| 5,331,073 A | 7/1994 | Weinschenk, III et al. | |
| 5,470,932 A | 11/1995 | Jinkerson | |
| 5,603,774 A | 2/1997 | LeBoeuf et al. | |
| 5,693,095 A | 12/1997 | Freeman et al. | |
| 6,653,422 B2 | 11/2003 | Freeman et al. | |
| 6,703,466 B1 * | 3/2004 | Karakelle et al. | 526/259 |
| 6,713,583 B2 | 3/2004 | Liao et al. | |
| 7,585,900 B2 | 9/2009 | Cordova et al. | |
| 7,714,039 B2 | 5/2010 | Cordova et al. | |
| 8,058,323 B2 | 11/2011 | Cordova et al. | |
| 2002/0107337 A1 * | 8/2002 | Rosenzweig et al. | 525/474 |
| 2008/0021548 A1 | 1/2008 | Cordova et al. | |
| 2009/0023876 A1 * | 1/2009 | Nunez et al. | 526/213 |
| 2009/0088493 A1 | 4/2009 | Laredo et al. | |
| 2009/0088544 A1 | 4/2009 | Laredo | |
| 2009/0093603 A1 * | 4/2009 | Schlueter | 526/304 |
| 2009/0093604 A1 | 4/2009 | Schlueter | |
| 2011/0003910 A1 | 1/2011 | Laredo | |
| 2011/0178202 A1 | 7/2011 | Laredo | |
| 2011/0313518 A1 | 12/2011 | Laredo et al. | |

OTHER PUBLICATIONS

PCT/US2012/040517, International Search Report, Date of mailing: Aug. 27, 2012.

* cited by examiner

*Primary Examiner* — Robert S Loewe

(74) *Attorney, Agent, or Firm* — Patrick M. Ryan

(57) ABSTRACT

Disclosed are low-tack, hydrophobic, high refractive index, acrylic materials. These materials, especially useful as intraocular lens materials, contain one or more aryl acrylic hydrophobic monomers as principal device-forming monomers, a tack-reducing macromer additive and a glistening-reducing additive. In addition to their use as intraocular lens materials, the present materials are also suitable for use in other implantable ophthalmic devices.

19 Claims, No Drawings

HYDROPHOBIC ACRYLIC INTRAOCULAR LENS MATERIALS

CROSS-REFERENCE TO RELATED APPLICATIONS

This application claims priority under 35 U.S.C. §119 to U.S. Provisional Patent Application No. 61/493,114, filed Jun. 3, 2011, the entire contents of which are incorporated herein by reference.

FIELD OF THE INVENTION

This invention is directed to acrylic device materials. In particular, this invention relates to low-tack, high refractive index acrylic device materials particularly suited for use as intraocular lens ("IOL") materials.

BACKGROUND OF THE INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a higher refractive index than silicone materials and unfold more slowly or controllably than silicone materials.

U.S. Pat. No. 5,290,892 discloses high refractive index, acrylic materials suitable for use as an IOL material. These acrylic materials contain, as principal components, two aryl acrylic monomers. They also contain a cross-linking component. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

U.S. Pat. No. 5,693,095 discloses foldable ophthalmic lens materials comprising a total of at least 90% by weight of only two principal lens-forming monomers. One lens-forming monomer is an aryl acrylic hydrophobic monomer. The other lens-forming monomer is a hydrophilic monomer. The lens materials also comprise a cross-linking monomer and optionally comprise a UV absorber, polymerization initiators, reactive UV absorbers and reactive blue-light absorbers.

U.S. Pat. No. 6,653,422 discloses foldable ophthalmic lens materials consisting essentially of a single device-forming monomer and at least one cross-linking monomer. The materials optionally contain a reactive UV absorber and optionally contain a reactive blue-light absorber. The single device-forming monomer is present in an amount of at least about 80% by weight. The device-forming monomer is an aryl acrylic hydrophobic monomer.

Some foldable acrylic materials are tacky. Foldable ophthalmic lenses made of tacky acrylic materials are difficult to handle. Attempts have been made to reduce tackiness so that the lenses are easier to process or handle, easier to fold or deform, and have shorter unfolding times. For example, U.S. Pat. No. 6,713,583 discloses ophthalmic lenses made of a material that includes branched chain alkyl groups in an amount effective to reduce tackiness. U.S. Pat. No. 4,834,750 discloses intraocular lenses made from materials that optionally include a fluoroacrylate component to reduce surface tackiness. U.S. Pat. No. 5,331,073 discloses acrylic materials that optionally include a hydrophilic component that is present in an amount sufficient to reduce the materials' tackiness. U.S. Pat. No. 5,603,774 discloses a plasma treatment process for reducing the tackiness of a soft acrylic article. U.S. Pat. No. 7,585,900 discloses the use of a dimethylacryloxypropyl-terminated polydimethylsiloxane macromer as a tack-reducing additive for certain acrylic ophthalmic device materials, including IOL materials.

SUMMARY OF THE INVENTION

Improved soft, foldable acrylic materials which are particularly suited for use as IOLs, but which are also useful as other implantable ophthalmic devices, such as keratoprostheses, corneal rings, corneal implants, and corneal inlays have now been discovered. These materials contain at least one principal lens-forming component, which is an aryl acrylic hydrophobic monomer, in an amount of 40-80% by weight. The materials also contain 0.1-3.9% by weight of a dimethacryloxypropyl-terminated polydimethylsiloxane macromer. Importantly, in order to reduce or eliminate haze and produce a clear, optically acceptable material, the copolymeric materials of the present invention contain 5-30% by weight of a siloxane monomer, and 3-20% by weight of a hydrophilic additive to reduce glistenings. The material also comprises a cross-linking monomer, a UV-light absorbing compound, and optionally a blue-light absorbing compound. The resulting copolymeric device materials are hydrophobic, which as used herein means that they have an equilibrium water content at 35° C. of 4% or less, preferably 3% or less, and more preferably 2.5% or less.

For IOLs, it is not enough that they have low tack as they need to be optically clear as well. The implantable ophthalmic device materials of the present invention are optically clear such that they are suitable for use as IOLs and they have low tack, low surface scatter, and good delivery properties. Among other factors, the present invention is based on the finding that a multi-component, copolymeric, high refractive index device material to obtained by copolymerizing the ingredients mentioned above is soft, glistening-free, has low tack and low haze, has low surface light scatter, and is capable of going through small (2.5 mm or less) incisions with good unfolding properties.

DETAILED DESCRIPTION OF THE INVENTION

Unless indicated otherwise, all component amounts are presented on a % (w/w) basis ("wt. %").

The ophthalmic device materials of the present invention comprise at least one principal device-forming monomer. For convenience, the device-forming monomer may be referred to as a lens-forming monomer, particularly with reference to an IOL. The materials of the present invention, however, are also suitable for use as other implantable ophthalmic devices such as such as keratoprostheses, corneal rings, corneal implants, and corneal inlays.

The aryl acrylic hydrophobic monomers suitable for use as principal lens-forming monomers in the materials of the present invention have the formula

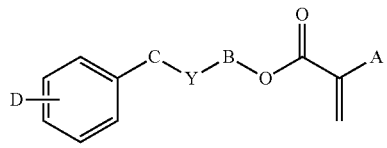

(I)

wherein:
A is H;
B is $(CH_2)_m$, $S(CH_2)_u$, $O(CH_2)_v$, or $[O(CH_2)_2]_n$;
u is 1-4;
v is 1-4;
C is $(CH_2)_w$;
m is 1-6;
n is 1-10;
Y is nothing, O, S, or NR, provided that if Y is O, S, or NR, then B is $(CH_2)_m$;
R is H, $CH_3$, $C_nH_{2n+1}$ (n=1-10), iso-$OC_3H_7$, $C_6H_5$, or $CH_2C_6H_5$;
W is 0-6, provided that m+w≤8; and
D is H, $C_1$-$C_4$ alkyl, $C_1$-$C_4$ alkoxy, $C_6H_5$, $CH_2C_6H_5$, Br, F, Cl, or I.

Preferred aryl acrylic hydrophobic monomers for use in the materials of the present invention are those wherein B is $(CH_2)_m$, m is 1-5, Y is nothing, O, or S, w is 0-1, and D is H. Most preferred are benzyl acrylate, 2-phenylethyl acrylate, 2-phenoxyethyl acrylate, 4-phenylbutyl acrylate, 5-phenylpentyl acrylate, 2-benzyloxyethyl acrylate, 3-benzyloxypropyl acrylate, 3-phenylpropyl acrylate, 3-phenoxypropyl acrylate, 2-(phenylthio)propyl acrylate, and 2-(phenylthio)ethyl acrylate. In one embodiment, the materials of the present invention comprise only one principal lens-forming monomer. In another embodiment, the materials of the present invention comprise two principal lens-forming monomers. Particularly preferred lens-forming monomers are 2-phenylethyl acrylate; 2-phenoxyethyl acrylate; benzyl acrylate; and 2-(phenylthio)ethyl acrylate.

Monomers of structure I can be made by known methods. For example, the conjugate alcohol of the desired monomer can be combined in a reaction vessel with methyl acrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding acrylic acid to the conjugate alcohol and catalyzing with a carbodiimide or mixing the conjugate alcohol with acryloyl chloride and a HCl acceptor such as pyridine or triethylamine.

The materials of the present invention comprise 40-80%, preferably is 40-74%, and more preferably 50-72% of the principal lens-forming monomer(s).

In addition to the principal lens-forming monomer, the materials of the present invention contain a macromer additive of formula (II) in an amount sufficient to reduce the material's tackiness. Generally, the amount of macromer additive in the materials of the present invention will range from 0.1-3.9% (w/w), and preferably will range from 1-3% (w/w), most preferably 1.5-2.5% (w/w). The macromer is a dimethylacryloxypropyl-terminated polydimethylsiloxane macromer of the formula:

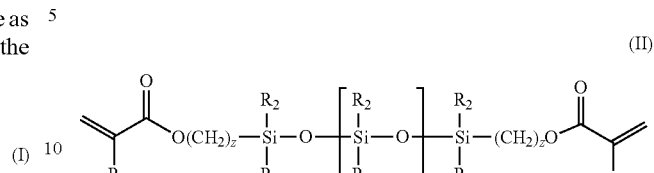

(II)

wherein
$R_1$ and $R_2$ are independently —$CH_3$, —$CH_2CH_3$, —$CH_2CH_2CH_2CH_3$, $CH_2CH_2CH_2CH_3$, —$C_6H_5$, —$CH_2C_6H_5$, —$CH_2CH_2C_6H_5$, —$CH_2CH_2CH_2C_6H_5$, or —$CH_2CH_2CH_2CH_2C_6H_5$;
$R_3$ is H, $CH_3$, or $CH_2CH_3$;
z is 2-11; and
x indicates the number of repeating units and determines the molecular weight of the macromer.

Preferred macromers of formula (II) are those wherein
$R_1=R_2=CH_3$;
$R_3$ is H, $CH_3$, or $CH_2CH_3$; and
z=3; and
x=0-43.

More preferred macromers of formula (II) are those wherein $R_1$, $R_2$, $R_3$, and z are as defined above for the preferred macromers and x is 0-22. In one embodiment, x is 5-14 (generally corresponding to a macromer molecular weight ($M_n$) of 800-1400). In another embodiment, x is 2-5 (generally corresponding to a macromer molecular weight ($M_n$) of 550-700).

Dimethylacryloxypropyl-terminated polydimethylsiloxanes of formula (II) ("PDMS"), also known as methacryloxypropyl terminated polydimethyl siloxanes, can be made by known methods. Some PDMS compounds are commercially available from Gelest, Inc. in molecular weights ($M_n$) ranging from 800-1400 (mid-range $M_n$ estimated as 1000). There are higher ($M_n$ 4K-6K, 5K-20K, 20K-30K) and lower ($M_n$ 386, 550-700) molecular weight grades of dimethacryloxypropyl-terminated siloxane commercially available. The macromer additive selection is limited by solubility (in the remainder of the copolymer material formulation) and formulation clarity (the copolymer material should be clear). Generally, PDMS used in the present invention will have a molecular weight ($M_n$) of about 300-about 3500 and preferably about 350-about 2000. In one embodiment, an especially preferred PDMS has a $M_n$ from about 800-about 1400. In another embodiment, an especially preferred PDMS has a $M_n$ from about 550-about 700.

In order to make the macromer of formula II and other components compatible in the final composition, the materials of the present invention contain 5-30%, preferably 5-25%, and most preferably 5-15% of a siloxane monomer of formula (III).

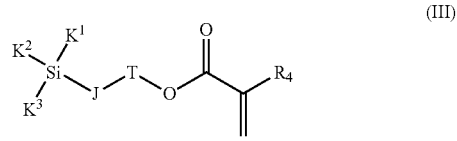

(III)

wherein
R$_4$ is H or CH$_3$;
T is nothing, O(CH$_2$)$_b$, or OCH$_2$CH(OH)CH$_2$;
b is 1-3;
J is (CH$_2$)$_z$; and
K$^1$, K$^2$, and K$^3$ independently are CH$_3$, C$_6$H$_5$, or OSi(CH$_3$)$_3$.

Monomers of structure (III) may be made by known methods and in some cases are commercially available. Preferred monomers of structure (III) are those wherein R$_4$ is CH$_3$, T is nothing or OCH$_2$CH(OH)CH$_2$, J is (CH$_2$)$_3$, and K$^1$, K$^2$, and K$^3$ independently are CH$_3$, C$_6$H$_5$, or OSi(CH$_3$)$_3$.

Most preferred monomers of structure (III) are those selected from the group consisting of:
3-[tris(trimethylsilyloxy)silyl]-propyl methacrylate ("TRIS");
3-(methacryloxy-2-hydroxypropoxy)propylmethylbis(trimethoxy)silane (SiMA);
methacryloxypropylpentamethyldisiloxane;
3-methacryloxypropylbis(trimethylsiloxy)methylsilane;
methacryloxymethyltris(trimethylsiloxy)silane;
(methacryloxymethyl)phenyl-dimethylsilane; and
(methacryloxymethyl)bis(trimethylsiloxy)methylsilane.

In order to reduce glistening, the materials of the present invention also contain a hydrophilic monomer selected from the group consisting of: hydroxy(C$_2$-C$_4$ alkyl)methacrylates, glycerol methacrylate, and N-vinyl pyrrolidone (NVP). Hydroxy(C$_2$-C$_4$ alkyl)methacrylates are preferred. The most preferred hydrophilic monomer is 2-hydroxyethyl methacrylate. The materials of the present invention contain a total amount of hydrophilic monomer of 5-30%, preferably 10-20%, and most preferably 13-20%. In one embodiment the materials of the present invention contain at least one hydrophilic monomer selected from the list recited above and at least one hydrophilic monomer of a different type, such as poly(ethylene glycol) monomethyl ether macromer (Mn~4100 Daltons) or the monomers and macromers described in U.S. Published Patent Application Nos. 20090088493, 20090088544, and 20090093604, respectively. Regardless of their identities, the total amount of hydrophilic monomers contained in the materials of the present invention should be limited such that the equilibrium water content (at 35° C.) of the polymerized device material of the present invention is less than 4%.

The copolymer materials of the present invention are cross-linked. The copolymerizable cross-linking agent used in the copolymers of this invention may be any terminally ethylenically unsaturated compound having more than one unsaturated group. Suitable cross-linking agents include, for example low molecular weight cross-linking agents having a molecular weight from 100-500 Daltons and high molecular weight cross-linking agents having a molecular weight from 501-6,000 Daltons. Low molecular cross-linking agents will typically be present in a total amount from 0.5-3%, whereas high molecular weight cross-linking agents will typically be present in a total amount from 2-10%. In general, the total amount of cross-linking agent in the materials of the present invention will range from 0.5-10%, and will preferably range from 1-3%. For purposes of determining the total amount of cross-linker in the present invention, the macromer of formula (II) is not considered to be part of the cross-linking component and is ignored. Suitable low molecular weight cross-linking agents include: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; triethylene glycol dimethacrylate; and their corresponding acrylates. Preferred low molecular cross-linking monomers include 1,4-butanediol dimethacrylate and triethylene glycol dimethacrylate. Suitable high molecular weight cross-linking agents include poly(ethylene glycol) diacrylate (M$_n$=700 Daltons) and poly(ethylene glycol) dimethacrylate (M$_n$=2000 Daltons).

In a preferred embodiment, the materials of the present invention contain 0.5-2% triethyleneglycol dimethacrylate (TEGDMA).

In addition to the aryl acrylic hydrophobic lens-forming monomer component, the macromer of formula (II), the hydrophilic additive to reduce glistenings, the siloxane monomer, and the cross-linking component, the lens materials of the present invention also contain reactive UV and/or blue-light absorbers.

Many reactive UV absorbers are known. Preferred reactive UV absorbers are 2-(2'-hydroxy-3'-methallyl-5'-methylphenyl)benzotriazole, commercially available as o-Methallyl Tinuvin P ("oMTP") from Polysciences, Inc., Warrington, Pa., and 3-(2H-benzo[d][1,2,3]triazol-2-yl)-4-hydroxyphenylethyl methacrylate ("Norbloc 7966"). UV absorbers are typically present in an amount from about 0.1-5% (w/w). In one embodiment, the materials of the present invention contain 1.5-2.5%, preferably 1.5-2%, of a reactive UV absorber.

Many reactive blue-light absorbing compounds are known. Preferred reactive blue-light absorbing compounds are those described in U.S. Pat. No. 5,470,932, U.S. Published Patent Application No. 20110003910, and in co-pending, commonly assigned U.S. patent application Ser. No. 13/008,409. the entire contents of which are hereby incorporated by reference. A preferred blue-light absorbing dye is N-2-[3-(2'-methylphenylazo)-4-hydroxyphenyl]ethyl methacrylamide. Blue-light absorbers are typically present in an amount from about 0.01-1% (w/w), preferably 0.02-0.5% (w/w).

The implantable ophthalmic device materials of the present invention are prepared by combining the ingredients described above and polymerizing the resulting mixture. Suitable polymerization initiators include thermal initiators and photoinitiators. Preferred thermal initiators include peroxy free-radical initiators, such as 2,2'-(diazene-1,2-diyl)bis (2,4-dimethylpentanenitrile; t-butyl (peroxy-2-ethyl)hexanoate; and di-(tert-butylcyclohexyl) peroxydicarbonate (commercially available as Perkadox® 16 from Akzo Chemicals Inc., Chicago, Ill.). A preferred photoinitiator is phenylphosphorylbis(mesitylmethanone), which is commercially available as lrgacure 819. Initiators are typically present in an amount of about 5% (w/w) or less, and preferably about 1% or less. Customarily, the total amount of initiator is not included when determining the amounts of other ingredients in copolymeric compositions.

The identity and amount of the principal lens-forming monomer component described above and the identity and amount of any additional components are determined by the desired properties of the finished ophthalmic lens. Preferably, the ingredients and their proportion are selected so that the acrylic lens materials of the present invention possess the following properties, which make the materials of the present invention particularly suitable for use in IOLs which are to be inserted through incisions of 2.5 mm or less, and preferably 2.0 mm or less.

The lens material preferably has a refractive index in the dry state of at least about 1.50 as measured by an Abbe' refractometer at 589 nm (Na light source). For a given optic diameter, optics made from materials having a refractive index lower than 1.50 are necessarily thicker than optics of the same power which are made from materials having a higher refractive index. As such, IOL optics made from materials having a refractive index lower than about 1.50 generally require relatively larger incisions for IOL implantation.

The glass-transition temperature ("Tg") of the lens material, which affects the material's folding and unfolding characteristics, is preferably below about 25° C., and more preferably below about 15° C. Tg is measured by differential scanning calorimetry at 10° C./min., and is determined as the half-height of the heat capacity increase.

The lens material will have an elongation (strain at break) of at least 100%, preferably at least 125%, and most preferably at least 150%. This property indicates that the lens generally will not crack, tear or split when folded. Elongation of polymer samples is determined on dumbbell shaped tension test specimens with a 20 mm total length, length in the grip area of 11 mm, overall width of 2.49 mm, 0.833 mm width of the narrow section, a fillet radius of 8.83 mm, and a thickness of 0.9 mm. Testing is performed on samples at standard laboratory conditions of 23±2° C. and 50±5% relative humidity using a tensile tester. The grip distance is set at 11 mm and a crosshead speed is set at 500 mm/minute and the sample is pulled to failure. The strain at break is reported as a fraction of the displacement at failure to the original grip distance. Stress at break is calculated at the maximum load for the sample, typically the load when the sample breaks, assuming that the initial area remains constant. The Young's modulus is calculated from the instantaneous slope of the stress-strain curve in the linear elastic region. The 25% secant modulus is calculated as the slope of a straight line drawn on the stress-strain curve between 0% strain and 25% strain. The 100% secant modulus is calculated as the slope of a straight line drawn on the stress-strain curve between 0% strain and 100% strain.

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

The invention will be further illustrated by the following examples, which are intended to be illustrative, but not limiting.

Example 1

IOL Formulations

The formulations shown in Tables 1-3 were prepared. Single piece IOLs and rectangular test samples measuring 20×10×0.9 mm (length×width×thickness) were made via thermal or photo-curing. Thermally cured samples were cured using a 70° C.→110° C. cure cycle. In brief, samples were 1) ramp heated from ambient temperature to 70° C. over 15 minutes, 2) soaked at 70° C. for 1 hour, 3) ramp heated from 70° C. to 110° C. over 20 minutes, and 4) soaked at 110° C. for 2 hours. Photo-cured samples were cured by pre-heating test samples in a nitrogen filled glove box for 10 minutes at 55° C. followed by irradiation with a Philips TLK 40 W/03 24-inch fluorescent lamp for 60 minutes. Cured samples were extracted in acetone for 20 hours at ambient temperature, dried slowly at ambient temperature for 20 hours, and then vacuum dried at low pressure (0.1 mm Hg) for a minimum of 20 hours at 70° C. As shown in Tables 1-3, a wide range of aliphatic and aromatic monomers, macromers, and polymers were used in attempts to improve the compatibility of the PDMS-DMA to give optically clear lenses.

Percent extractables and clarity are shown in Table 4. Clarity was qualitatively assessed on hydrated lenses using a Dolan-Jenner Fiber-Lite Fiber Optic Illuminator (model 190). Dry and hydrated lenses were placed in the light path while rotating the samples in the x, y, and z directions to determine relative haze. Glistening evaluation was carried out by placing samples in deionized water at 45° C. for 20 hours and then cooling to ambient temperature. Samples were inspected for glistenings after 2 hours of cooling to ambient temperature using an optical microscope under dark field conditions with a magnification of 100×. All clear samples contained less than 10 glistenings per location. Glistenings could not be detected in samples that were allowed to equilibrate in water or BSS saline solution for approximately 1 week.

TABLE 1

| Component | Example (% w/w) | | | | | | |
|---|---|---|---|---|---|---|---|
| | 1A | 1B | 1C | 1D | 1E | 1F | 1G |
| PEA | 74.1 | 76.4 | 70.4 | 73.0 | 75.6 | 66.8 | 69.2 |
| PDMS-DMA | 2.58 | 2.52 | 2.42 | 2.46 | 2.46 | 2.09 | 2.01 |
| TRIS | — | — | — | — | — | 10.0 | 10.0 |
| HEMA | 15.2 | 15.0 | 15.0 | 15.1 | 15.0 | 15.0 | 13.0 |
| HEA | 5.11 | — | — | — | — | — | — |
| pPEG1 | — | — | — | — | — | — | 2.63 |
| PEG4000-DA | — | — | — | — | — | 3.01 | — |
| PEG2000-DMA | — | 3.02 | — | — | — | — | — |
| PEG1000-DMA | — | — | 10.2 | 7.47 | 4.94 | — | — |
| EGDMA | 0.51 | — | — | — | — | — | — |
| BDDA | 0.50 | 1.05 | — | — | — | 1.01 | 1.19 |
| TEGDMA | — | — | — | — | — | — | — |
| Norbloc | 1.99 | 2.01 | 2.01 | 2.04 | 2.04 | 2.01 | 1.99 |
| V-65 | 1.03 | — | — | — | — | — | — |
| Irg819 | — | 0.25 | 0.24 | 0.24 | 0.23 | 0.25 | 0.25 |

PDMS-DMA = methacryloxypropyl terminated polydimethylsiloxane (MW = 900-1200)
Norbloc = 3-(2H-benzo[d][1,2,3]triazol-2-yl)-4-hydroxyphenethyl methacrylate
Irg819 = phenylphosphorylbis(mesitylmethanone)
PEA = 2-phenylethyl acrylate
HEMA = 2-hydroxyethylmethacrylate
BDDA = butane-1,4-diyl diacrylate
EGDMA = ethyleneglycol dimethacrylate
TRIS = 3-[tris(trimethylsilyloxy)silyl]-propyl methacrylate
PEG4000-DA = poly(ethylene glycol) diacrylate (Mn = 4000)
PEG2000-DMA = poly(ethylene glycol) dimethacrylate (Mn = 2000)
PEG1000-DMA = poly(ethylene glycol) dimethacrylate (Mn = 1000)
pPEG1 = poly[poly(ethylene glycol)monomethyl ether methacrylate, Mn = 550], vinyl functionalized prepolymer (Mn = 4100)

TABLE 2

| Component | Example (% w/w) | | | | | | |
|---|---|---|---|---|---|---|---|
| | 1H | 1I | 1J | 1K | 1L | 1M | 1N |
| PEA | 60.7 | 68.6 | 56.0 | 66.1 | 62.3 | 73.2 | 71.5 |
| PEMA | — | — | 25.8 | — | — | — | — |
| PDMS-DMA | 2.43 | 1.97 | 2.05 | 1.98 | 2.12 | 1.20 | 2.0 |
| TRIS | 10.0 | 10.0 | 10.0 | 10.0 | 10.0 | — | 10.0 |
| HEMA | 15.1 | 14.0 | — | 13.0 | 14.9 | 15.0 | 10.0 |
| pPEG1 | — | — | 3.12 | — | 2.65 | 2.51 | 3.0 |
| PEG4000-DA | — | 2.47 | — | — | — | — | — |
| PEG2000-DMA | — | — | — | 3.00 | — | — | — |
| PEG1000-DMA | 9.69 | — | — | — | — | — | — |
| PEG700-DA | — | — | — | 3.90 | — | — | — |
| PPG900-DA | — | — | — | — | 5.96 | 6.15 | — |

TABLE 2-continued

| Component | Example (% w/w) | | | | | | |
|---|---|---|---|---|---|---|---|
| | 1H | 1I | 1J | 1K | 1L | 1M | 1N |
| BDDA | — | 0.92 | 1.04 | — | — | — | 0.5 |
| TEGDMA | — | — | — | — | — | — | 1.0 |
| Norbloc | 2.02 | 2.02 | 2.01 | 2.02 | 2.00 | 2.01 | 2.0 |
| Irg819 | 0.25 | 0.22 | 0.25 | 0.24 | 0.25 | 0.25 | 0.25 |

PEMA = 2-phenylethyl methacrylate
TEGDMA = triethyleneglycol dimethacrylate
PPG900-DA = polypropylene glycol diacrylate (Mn = 900)
PEG700-DA = poly(ethylene glycol) diacrylate (Mn = 700)

TABLE 3

| Component | Example (% w/w) | | | | | |
|---|---|---|---|---|---|---|
| | 1O | 1P | 1Q | 1R | 1S | 1T |
| PEA | 60.0 | 68.7 | 62.7 | 73.7 | 68.2 | 67.9 |
| PhDMS-MA | 32.5 | — | — | — | — | — |
| PDMS-DMA | 1.0 | 2.0 | 2.0 | 1.0 | 2.0 | — |
| P3D | — | — | — | — | — | 1.25 |
| TRIS | — | 10.0 | 10.0 | — | 10.0 | 10.0 |
| HEMA | — | 14.0 | 15.0 | 15.0 | 15.0 | 15.0 |
| pPEG2 | 3.0 | — | 2.5 | 2.5 | — | 2.5 |
| PEG4000-DA | — | 2.5 | — | — | 3.00 | — |
| PPG900-DA | — | — | 6.0 | 6.0 | — | — |
| BDDA | 0.5 | 1.0 | — | — | — | — |
| TEGDMA | 1.0 | — | — | — | — | 1.5 |
| Norbloc | 2.0 | — | — | — | — | — |
| oMTP | — | 1.8 | 1.8 | 1.8 | 1.8 | 1.8 |
| BB | — | 0.04 | 0.04 | 0.04 | 0.04 | 0.04 |
| Irg819 | 0.25 | 0.20 | 0.20 | 0.20 | 0.20 | 0.20 |

PhDMS-MA = (dimethyl(phenyl)silyl)methyl methacrylate
P3D = Acryloxy terminated ethyleneoxide-dimethylsiloxane-ethyleneoxide ABA block copolymer (1500-1600 Daltons, 45-55 wt. % ethylene oxide)
pPEG2 = poly[poly(ethylene glycol)monomethyl ether methacrylate, Mn = 350], vinyl functionalized prepolymer (Mn = 4200)
oMTP = ortho-methallyl Tinuvin P = 2-(2H-benzo[d][1,2,3]triazol-2-yl)-4-methyl-6-(2-methylallyl)phenol
BB = N-(4-hydroxy-3-(o-tolyldiazenyl)phenethyl)methacrylamide

TABLE 4

| Example | % Extractables (N ≥ 6) | Clarity, post polymerization | Clarity, post 45 - 22° C. ΔT test |
|---|---|---|---|
| 1A | 2.5 ± 0.1 | Clear | Hazy |
| 1B | 1.4 ± 0.1 | Clear | Clear |
| 1C | 1.2 ± 0.1 | Hazy | Clear |
| 1D | 1.3 ± 0.1 | Hazy | Clear |
| 1E | 1.9 ± 0.1 | Hazy | Clear |
| 1F | 1.7 ± 0.2 | Clear | Clear |
| 1G | 1.6 ± 0.1 | Clear | Clear |
| 1H | 1.4 ± 0.1 | Hazy | Clear |
| 1I | 1.3 ± 0.1 | Clear | Clear |
| 1J | 1.9 ± 0.1 | ²Hazy | Hazy |
| 1K | 1.5 ± 0.1 | Clear | Clear |
| 1L | — | Clear | Clear |
| 1M | — | Clear | Clear |
| 1N | — | Clear | Clear |
| 1O | — | Hazy | Hazy |
| 1P | 2.8 ± 0.1 | Hazy | Hazy |
| 1Q | 3.1 ± 0.2 | Clear | Clear |
| 1R | 2.5 ± 0.1 | Clear | Clear |
| 1S | 6.0 ± 0.4 | Clear | Clear |
| 1T | 3.4 ± 0.1 | Clear | Clear |

Example 2

Tack Study

Certain compositions from Examples 1A-1T were tested for tack using a modified tensilometry test method which measures polymer to metal tack. Tack values greater than 52 N were considered to have high tack and could not be accurately measured using the given load cell. Tack values between 40-52 N were considered to be moderate to high. Tack values between 30-40 N were considered to be acceptable. Tack values between 20-30 N were considered to be low. This general classification of tack values is subjective and acts only as a guideline for predicting polymer to metal tack. It cannot be used to predict lens delivery performance. The successful delivery of a lens will be dependent on many factors including lens composition, how it was processed (eg., surface modification), in addition to the properties of the delivery device.

Tack Testing Procedure

Tack testing was conducted on an Instron mechanical tester using a custom fixture for measuring the metal-polymer tack or adhesion. The fixture includes a highly polished stainless steel circular stationary pin of 8 mm in diameter that is affixed to the stationary portion of the load frame. The upper (moveable) section of the load frame crosshead is attached to a circular metal platform with a hole in the center. The moveable crosshead is lowered until the bottom pin appears through the hole in the center of the upper fixture and the crosshead movement is stopped when the pin is slightly above the metal platform. The polymer sample is then placed on the protruding pin. A fresh 10 mm diameter disk is press cut from the polymer sample and is placed on the top of the protruding pin. A 300 gram weight is placed on top of the sample, pressing the sample to the pin with a uniform load. One minute after placing the weight on the sample, the Instron mechanical tester is started with a separation rate of 5 mm/min. Data is collected at a rate of 5 points/sec until the sample is pulled up off of the pin. The maximum force and area under the curve (work energy) is recorded.

Results

Six samples of each material were tested for pre-extraction tack and the results averaged. The values are given in Table 5 along with +1 standard deviation bars. The pre-extraction tack values shown in Table 5 are generally less reliable than post-extraction tack values because of plasticization effects of non-reacted starting material, which is different for each formulation. Thus, it is generally considered that the tack results shown in Table 5 represent the highest tack values that can be expected for a given formulation.

TABLE 5

| Example | Max Load (N) |
|---|---|
| 1A | — |
| 1B | 40 ± 3 |
| 1C | 38 ± 3 |
| 1D | 30 ± 1 |
| 1E | 32 ± 1 |
| 1F | >52 |
| 1J | 43 ± 8 |
| 1Q | 50 ± 5 |
| 1R | >52 |

Example 3

Tensile Testing

The tensile properties of extracted test samples were measured using an Instron tensilometer and results are shown in Table 6.

TABLE 6

| Example (N ≥ 3) | Stress at Break (MPa) | Strain at Break (%) | Young's Modulus (MPa) | 25% Secant Modulus (MPa) | 100% Secant Modulus (MPa) |
| --- | --- | --- | --- | --- | --- |
| 1F | 5.0 ± 0.2 | 168 ± 4 | 22.0 ± 0.5 | 3.11 ± 0.04 | 2.10 ± 0.02 |
| 1G | 3.4 ± 0.4 | 145 ± 8 | 21.0 ± 0.6 | 3.7 ± 0.1 | 1.97 ± 0.05 |
| 1H | 3.4 ± 0.5 | 137 ± 11 | 17.0 ± 0.8 | 3.11 ± 0.04 | 2.10 ± 0.02 |
| 1I | 3.7 ± 0.2 | 174 ± 3 | 20 ± 2 | 3.4 ± 0.2 | 1.68 ± 0.05 |
| 1J | 2.8 ± 0.2 | 153 ± 2 | 19 ± 1 | 2.95 ± 0.07 | 1.47 ± 0.03 |

Example 4

Surface Scatter Measurements

Excessive light scattering of IOL surfaces has been recently cited by several prominent surgeons in the field of ophthalmology as an undesirable trait associated with premium Acrysof IOLs. Scheimpflug photography is one method commonly used to quantify the amount of scattered light. In short, a Scheimpflug camera is used to capture an image of an implanted IOL. The scattered light intensity, measured in CCT values, can be subsequently quantified. To date, our target has been to develop lenses which exhibit <30 CCT after 10 years accelerated aging. In this study, 21 diopter single piece IOLs were made from formulations 1A-1O. The IOLs were first aged under accelerated conditions in BSS saline solution at 90° C., then rinsed in deionized water to remove the salts and then dried. Surface scatter measurements were carried out on samples hydrated in BSS saline solution for 20 hours at ambient temperature. In some cases, measurements were carried out on dry samples. As shown in Table 7, various lens formulations showed low surface scatter of less than 30 CCT requirement.

TABLE 7

| Example (N = 3) | CCT T = 10 yr (hydrated) | CCT T = 10 yr (dry) |
| --- | --- | --- |
| 1A | 28 ± 18 | <30 |
| 1B | 26.5 ± 4.5 | <30 |
| 1C | 18 ± 3 | 103 ± 14 |
| 1D | 12 ± 6 | 53 ± 35 |
| 1E | 16 ± 7 | <30 |
| 1F | 17 ± 3 | <30 |
| 1G | 18 ± 5 | <30 |
| 1H | 22 ± 21 | 136 ± 75 |
| 1I | 13.3 ± 1.3 | <30 |
| 1J | [1]160 ± 56 | — |
| 1K | 28 ± 5 | <30 |
| 1L | 10.7 ± 3.0 | <30 |
| 1M | 16 ± 8 | <30 |
| 1N | 26 ± 7 | <30 |
| 1O | [2]166 ± 28 | — |
| 1P | [3]75 ± 55 | — |
| 1Q | [3]138 ± 55 | — |
| 1R | [3]60 ± 36 | — |
| 1S | [4]47 ± 10 | — |
| 1T | [4]18 ± 5 | — |

[1]7 years simulated accelerated aging
[2]4 years simulated accelerated aging
[3]5 years simulated accelerated aging
[4]3 years simulated accelerated aging Example 6

Delivery Evaluation of Lenses

40-Diopter lenses from formulation 1L were delivered through Monarch III D cartridges using H4 handpieces and Viscoat viscoelastic. Lens delivery was carried out at 18° C. and 23° C. into 25° C. water without dwell time. Post-delivery evaluations included cartridge tip stress levels. In general, manual delivery forces for N=6 lenses were acceptable. No stuck haptics were observed post-delivery and optics unfolded within 2 seconds. Nozzle stress levels upon delivery were rated level 4 on a scale of 0-5. The somewhat high nozzle stress was attributed to excessive HEMA and crosslinker levels in formulation 1L which resulted in a relatively stiff material with low elongation. This may have also contributed to 1 out of 6 deliveries having a cracked leading haptic post-delivery. More recent compositions with lower Young's Modulus and higher % strain at break have resulted in nozzle stress values between 0-2 (data not shown) with desirable unfolding properties. The specific examples in this memorandum do not limit the scope of this invention and represent only small subset of material properties that can be obtained using the approach disclosed in this invention report. Further optimizations of select formulations will be carried out in future as we aim to develop IOLs that are best-in-class in all categories.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. A copolymeric ophthalmic device material formed by polymerizing a mixture comprising
   a) 40-80% (w/w) or more of an aryl acrylic hydrophobic monomer of formula (I)

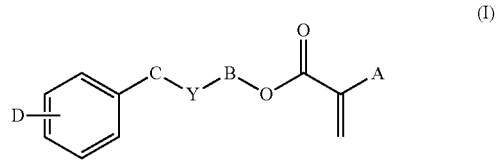

wherein:
A is H;
B is $(CH_2)_m$, $S(CH_2)_u$, $O(CH_2)_v$, or $[O(CH_2)_2]_n$;
u is 1-4;
v is 1-4;
C is $(CH_2)_w$;
m is 1-6;
n is 1-10;
Y is nothing, O, S, or NR, provided that if Y is O, S, or NR, then B is $(CH_2)_m$;
R is H, $CH_3$, $C_nH_{2n+1}$ (n=1-10), iso-$OC_3H_7$, $C_6H_5$, or $CH_2C_6H_5$;
w is 0-6, provided that m+w≤8; and
D is H, $C_1$-$C_4$ alkyl, $C_1$-$C_4$ alkoxy, $C_6H_5$, $CH_2C_6H_5$, Br, F, Cl, or I;
b) 0.1-3.9% (w/w) of a macromer of formula (II)

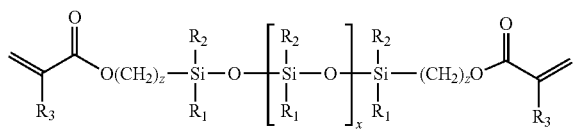

(II)

wherein
$R_1$ and $R_2$ are independently —$CH_3$, —$CH_2CH_3$, —$CH_2CH_2CH_2CH_3$, $CH_2CH_2CH_2CH_3$, —$C_6H_5$, —$CH_2C_6H_5$, —$CH_2CH_2C_6H_5$, —$CH_2CH_2CH_2C_6H_5$, or —$CH_2CH_2CH_2CH_2C_6H_5$;
$R_3$ is H, $CH_3$, or $CH_2CH_3$;
z is 2-11; and
x indicates the number of repeating units and determines the molecular weight of the macromer and is such that the macromer has a molecular weight of about 300-about 3500;
c) 5-30% (w/w) of a siloxane monomer of formula (III)

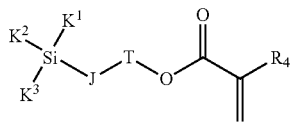

(III)

wherein
$R_4$ is H or $CH_3$;
T is nothing, $O(CH_2)_b$, or $OCH_2CH(OH)CH_2$;
b is 1-3;
J is $(CH_2)_z$; and
$K^1$, $K^2$, and $K^3$ independently are $CH_3$, $C_6H_5$, or $OSi(CH_3)$;
d) 5-30% (w/w) of a hydrophilic monomer selected from the group consisting of: hydroxy($C_2$-$C_4$ alkyl)methacrylates, glycerol methacrylate, and N-vinyl pyrrolidone;
e) a cross-linking monomer; and
f) a reactive UV absorber;
wherein the copolymeric ophthalmic device material has an equilibrium water content at 35° C. of less than 4%.

2. The copolymeric device material of claim 1 wherein the aryl acrylic hydrophobic monomer is selected from the group consisting of: benzyl acrylate; 2-phenylethyl acrylate; 2-phenoxyethyl acrylate; 4-phenylbutyl acrylate; 5-phenylpentyl acrylate; 2-benzyloxyethyl acrylate; 3-benzyloxypropyl acrylate; 3-phenylpropyl acrylate; 3-phenoxypropyl acrylate; 2-(phenylthio)propyl acrylate; and 2-(phenylthio)ethyl acrylate.

3. The copolymeric device material of claim 2 wherein the aryl acrylic hydrophobic monomer is selected from the group consisting of: 2-phenylethyl acrylate; 2-phenoxyethyl acrylate; benzyl acrylate; and 2-(phenylthio)ethyl acrylate.

4. The copolymeric device material of claim 1 wherein the mixture comprises 40-74% (w/w) of the aryl acrylic hydrophobic monomer.

5. The copolymer device material of claim 4 wherein the mixture comprises 50-72% (w/w) of the aryl acrylic hydrophobic monomer.

6. The copolymeric device material of claim 1 wherein the mixture comprises 1-3% (w/w) of the macromer of formula (II).

7. The copolymeric device material of claim 6 wherein the mixture comprises 1.5-2.5% (w/w) of the macromer of formula (II).

8. The copolymeric device material of claim 1 wherein the macromer of formula (II) has a molecular weight of 350-2,000.

9. The copolymeric device material of claim 8 wherein the macromer of formula (II) has a molecular weight of 800-1,400.

10. The copolymeric device material of claim 8 wherein the macromer of formula (II) has a molecular weight of 550-700.

11. The copolymeric device material of claim 1 wherein the mixture comprises 5-25% (w/w) of the siloxane monomer of formula (III).

12. The copolymeric device material of claim 11 wherein the mixture comprises 5-15% (w/w) of the siloxane monomer of formula (III).

13. The copolymeric device material of claim 1 wherein the hydrophilic monomer is a hydroxy($C_2$-$C_4$ alkyl)methacrylate and the mixture comprises 10-20% (w/w) of the hydrophilic monomer.

14. The copolymeric device material of claim 13 wherein the hydrophilic monomer is 2-hydroxyethyl methacrylate and the mixture comprises 13-20% (w/w) of the hydrophilic monomer.

15. The copolymeric device material of claim 1 wherein the mixture comprises 0.5-10% (w/w) of the cross-linking agent.

16. The copolymeric device material of claim 15 wherein the mixture comprises 1-3% (w/w) of the cross-linking agent and the cross-linking agent is selected from the group consisting of: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; triethylene glycol dimethacrylate; and their corresponding acrylates.

17. The copolymeric device material of claim 16 wherein the cross-linking agent is selected from the group consisting of 1,4-butanediol dimethacrylate and triethylene glycol dimethacrylate.

18. The copolymeric device material of claim 1 wherein the mixture further comprises a reactive blue-light absorbing compound.

19. An intraocular lens comprising the copolymeric device material of claim 1.

* * * * *